(12) United States Patent
McWhirter et al.

(10) Patent No.: US 6,715,912 B2
(45) Date of Patent: Apr. 6, 2004

(54) SURFACE AERATION IMPELLERS

(75) Inventors: John R. McWhirter, Boalsburg, PA (US); Prakash G. Balan, Wilmington, DE (US)

(73) Assignees: The Penn State Research Foundation, University Park, PA (US); Mixing & Mass Transfer Technologies, LLC, State College, PA (US)

( * ) Notice: Subject to any disclaimer, the term of this patent is extended or adjusted under 35 U.S.C. 154(b) by 0 days.

(21) Appl. No.: 10/244,349

(22) Filed: Sep. 16, 2002

(65) Prior Publication Data

US 2003/0067839 A1 Apr. 10, 2003

Related U.S. Application Data

(63) Continuation-in-part of application No. 09/895,418, filed on Jul. 2, 2001, now Pat. No. 6,464,384, which is a continuation of application No. 09/358,502, filed on Jul. 21, 1999, now abandoned, which is a continuation of application No. 09/162,088, filed on Sep. 28, 1998, now Pat. No. 5,972,661.

(51) Int. Cl.[7] .............................. B01F 3/04; B01F 7/18
(52) U.S. Cl. ........................ 366/265; 366/317; 261/91; 416/186 R
(58) Field of Search ................................ 366/262, 279, 366/265, 263, 342, 343, 317, 102; 261/91; 416/186 R (56) References Cited

U.S. PATENT DOCUMENTS

| | | | |
|---|---|---|---|
| 3,290,016 A | * | 12/1966 | Lennon et al. ............... 366/317 |
| 3,341,450 A | * | 9/1967 | Ciabattari et al. ............ 261/91 |
| 3,479,017 A | | 11/1969 | Thikötter |
| 3,576,316 A | | 4/1971 | Kaelin |
| 3,610,590 A | | 10/1971 | Kaelin |
| 3,741,682 A | | 6/1973 | Robertson |
| 4,066,383 A | | 1/1978 | Lakin |
| 4,074,953 A | | 2/1978 | Budde et al. |
| 4,151,231 A | | 4/1979 | Austin et al. |
| 4,334,826 A | | 6/1982 | Connolly et al. |
| 4,548,765 A | * | 10/1985 | Hultholm et al. ........... 366/102 |
| 4,904,159 A | | 2/1990 | Wickoren |
| 5,522,989 A | | 6/1996 | Hove |
| 5,988,604 A | | 11/1999 | McWhirter |

OTHER PUBLICATIONS

McWhirter, et al. "Oxygen Mass Transfer Fundamentals of Surface Aerators," Industrial & Engineering Chemistry Research, vol.34, No. 8, pp. 2644–2654, 1995.

* cited by examiner

Primary Examiner—Tony G. Soohoo
(74) Attorney, Agent, or Firm—McQuaide, Blasko, Schwartz, Fleming & Faulkner, Inc.

(57) ABSTRACT

A surface aeration impeller for use in a liquid filled tank. The impeller is rotatable about an axis perpendicular to the static liquid surface. The impeller has a plurality of blades mounted on the underside of a disc or disc-like surface. Each blade has a multi-faceted or curved geometry ranging from vertical at the point of attachment to the disc to partially inclined at the bottom. The blades are spaced circumferentially about the axis and are disposed at acute angles to radial lines from the axis of rotation of the impeller. The lower portions of the blades, which are inclined but non-vertical, are positioned at or below the static liquid surface. When the impeller is rotated, the lower portion pumps the liquid up onto the vertical portion of the blades where the liquid is discharged into a spray umbrella in a direction upwardly and outwardly away from the impeller. The design of the invention produces substantially higher oxygen transfer efficiency and overall liquid pumping rates than prior art designs and is particularly useful in the aeration of sewage and other wastewater.

20 Claims, 3 Drawing Sheets

Fig.1

ROTATION
Fig. 2

SURFACE AERATION IMPELLERS

RELATED APPLICATIONS

This application is a Continuation-in-Part of application Ser. No. 09/895,418 filed Jul. 2, 2001, now U.S. Pat. No. 6,464,384 which is a Continuation of application Ser. No. 09/358,502, filed Jul. 21, 1999, now abandoned, which in a Continuation of application Ser. No. 09/162,088 filed Sep. 28, 1998, now U.S. Pat. No. 5,972,661.

FIELD OF THE INVENTION

The present invention relates generally to rotating impellers. More specifically, the invention relates to surface aeration impellers that rotate on a vertical axis near the surface of a body of liquid in a tank causing liquid to be sprayed into the gas above the liquid and gas to be entrained into the liquid by the liquid spray impinging onto the liquid surface.

BACKGROUND OF THE INVENTION

In a number of industrial processes it is desirable to enhance the mass transfer of a gas into a liquid. Much of this need results from biochemical oxidation processes which use aerobic microbes. Aerobic microbes are employed because they are able to convert a raw material into a higher value material. Some examples include aerobic fermentation processes for manufacturing fragrances, flavors, and pharmaceutical components. Perhaps an even more important process is the aeration of sewage and other wastewater streams. What all these processes using aerobic microbes have in common is the need for oxygen to be dissolved into the liquid in order for the microbes to be able to convert the raw material into the desired result. Since the microbes work most efficiently when there is an adequate level of dissolved oxygen available in the liquid, it is typically desirable to transfer additional amounts of oxygen or air into the liquid. This can be accomplished in a number of ways but the two most common techniques are gas sparging and surface aeration. In a gas sparging procedure, a gas (e.g. air or oxygen) is bubbled through the liquid in a manner that increases the amount of dissolved oxygen in the liquid. In contrast, surface aeration uses an impeller located at the surface of the liquid to agitate or spray the liquid into the gas. The spray subsequently impinges on the liquid surface which also entrains gas into the liquid surface.

One of the basic procedures for the treatment of sewage and other wastewater streams is known as the activated sludge process, which was discovered or invented more than seventy years ago. It is a biochemical type of reaction, involving the mass transfer of oxygen into water, and then the transfer and use of that dissolved oxygen to support the growth of aerobic microorganisms suspended in the water. These microorganisms, known as the biomass, oxidize the organic materials in the wastewater in different ways to eliminate the biochemical oxygen demand (BOD) of the wastewater.

The original activated sludge process involved introducing air from a blower through various forms of diffuser devices located in the bottom of the aeration tank or basin. These devices generally have low oxygen-transfer efficiency and poor solids-suspension characteristics. More than forty years ago, a different approach was taken to aeration in the activated sludge process. This different approach was known as mechanical surface aeration. This technique made use of a mechanical agitator operating at the liquid surface to throw or spray liquid into the air and to induce entrainment of air into the liquid surface, without the use of a compressor and the diffusers. Since that time, a fairly large number of different designs for surface aeration impellers have been introduced, both for the purpose of increasing the oxygen-transfer efficiency and also, secondarily, if possible, to improve liquid mixing and solids suspension. The problem of solids suspension, however, has an obvious limitation because of the remoteness of the surface aeration impeller from the tank bottom where the biomass solids tend to settle if the bulk liquid in the tank is not adequately mixed.

The standard measure of aeration efficiency is the number of pounds of oxygen transferred into the liquid per hour per horsepower of energy used to operate the aeration system. This measure is known as the Standard Aeration Efficiency (SAE). The SAE for current state of the art surface aeration devices ranges from about 2.0 to about 3.3 pounds of oxygen per hour per horsepower in the larger aerator sizes. In smaller sizes, the efficiency values can be somewhat higher. Since wastewater treatment plants are pure cost centers (i.e. they do not sell a product) and since electric power is one of the main operating costs in such a plant, the oxygen-transfer efficiency performance of such aerators is extremely important, especially in the larger plants. This need has led to a number of attempts at producing surface aeration impeller designs with greater oxygen transfer efficiency.

Typical of state of the art surface aeration impellers are those shown in U.S. Pat. No. 3,479,017 to Thikotter; U.S. Pat. Nos. 3,576,316 and 3,610,590 to Kaelin; and U.S. Pat. No. 3,741,682 to Robertson; U.S. Pat. No. 4,066,383 to Lakin; U.S. Pat. No. 4,074,953 to Budde et al.; U.S. Pat. No. 4,151,231 to Austin; U.S. Pat. No. 4,334,826 to Connolly et al.; U.S. Pat. No. 5,522,989 to Hove; and U.S. Pat. No. 5,988,604 to McWhirter. All of these patents are incorporated herein in their entirety.

Thikotter discloses a surface aeration impeller for use in an activated sludge process. Thikotter's aerator comprises a flat, circular impeller disc having a plurality of impeller blades depending from the undersurface of the disc. The blades are generally flat, positioned radially and have a height that decreases from its inner edge to its outer edge. This design principally focuses on spraying the liquid and does not provide much up-pumping action or mixing of the tank liquid content resulting in relatively low efficiency of the system. Robertson and Austin also disclose surface aeration impellers having multiple blades located on the underside of a disc. Their blades are radial or approximately radial and generally flat but have a horizontal plate secured to the lower edge of each blade. Again, these designs primarily focus on throwing or spraying of the liquid and do not provide much up-pumping action and mixing of the body of liquid in the tank.

Unlike Thikotter, Roberston, and Austin, Lakin and Connolly disclose various forms of surface aeration impellers having primarily vertically curved blades. Most seem to have multiple blades on a disc-shaped mounting member. Kaelin and Budde et al. also teach surface aerator designs. The blades of Budde et al. are radial and Kaelin show other designs representative of the state of the art. The design of Budde et al. does not provide much mixing action and Kaelin in addition suffers from the disadvantage of being difficult to manufacture.

Hove teaches a device and method for aerating wastewater. The device has multiple blades positioned on a disc-shaped mounting member. The blades appear to be entirely radial. Hove's blades are unique compared with the above patents in that they are located both above and below the disc-shaped mounting member.

McWhirter '604 teaches a surface aeration impeller that is an axial flow impeller that may have either pitched blade turbine or airfoil shaped blades. The blades of the McWhirter patent are not mounted to the underside of a disc-shaped mounting member Additionally, while the upper section of the '604 blades are not strictly radial, the lower section is radial (at least at one point). This impeller does provide some up-pumping and mixing action but still leaves room for improved liquid pumping and oxygen transfer efficiency.

Although such surface aeration devices as discussed above have functioned in a generally satisfactory manner, problems have been experienced with excessive splashing and misting, insufficient liquid pumping, mixing and circulation, and clogging of the impellers during operation. Accordingly, there continues to be a need for improved designs that increase the efficiency of the aeration process and/or address some of these problems. In particular, surface aeration impeller designs and operational characteristics that increase the oxygen transfer efficiency into the liquid and thereby reduce operating costs are especially desirable.

Many of the limitations associated with prior art surface aerator impeller designs result from an insufficient understanding of the fundamental mechanisms and fluid dynamics of surface aeration. The current state-of-the-art oxygen mass transfer analysis for surface aerators is essentially limited to the simple, idealized model employed in the ASCE Standard for the Measurement of Oxygen Transfer in Clean Water. This oversimplified and limited model has been used for decades to characterize the oxygen mass transfer performance of surface aerators. A more realistic and rigorous model has been developed by McWhirter et al. in "Oxygen Mass Transfer Fundamentals of Surface Aerators", Ind. Eng. Chem. Res. 34, 2644–2654, 1995. This mechanistic model provides a more physically realistic description of the actual oxygen transfer mechanisms of surface aerators and separates the oxygen mass transfer process into two distinct zones: a liquid spray mass transfer zone and a surface reaeration mass transfer zone.

Figure 4:
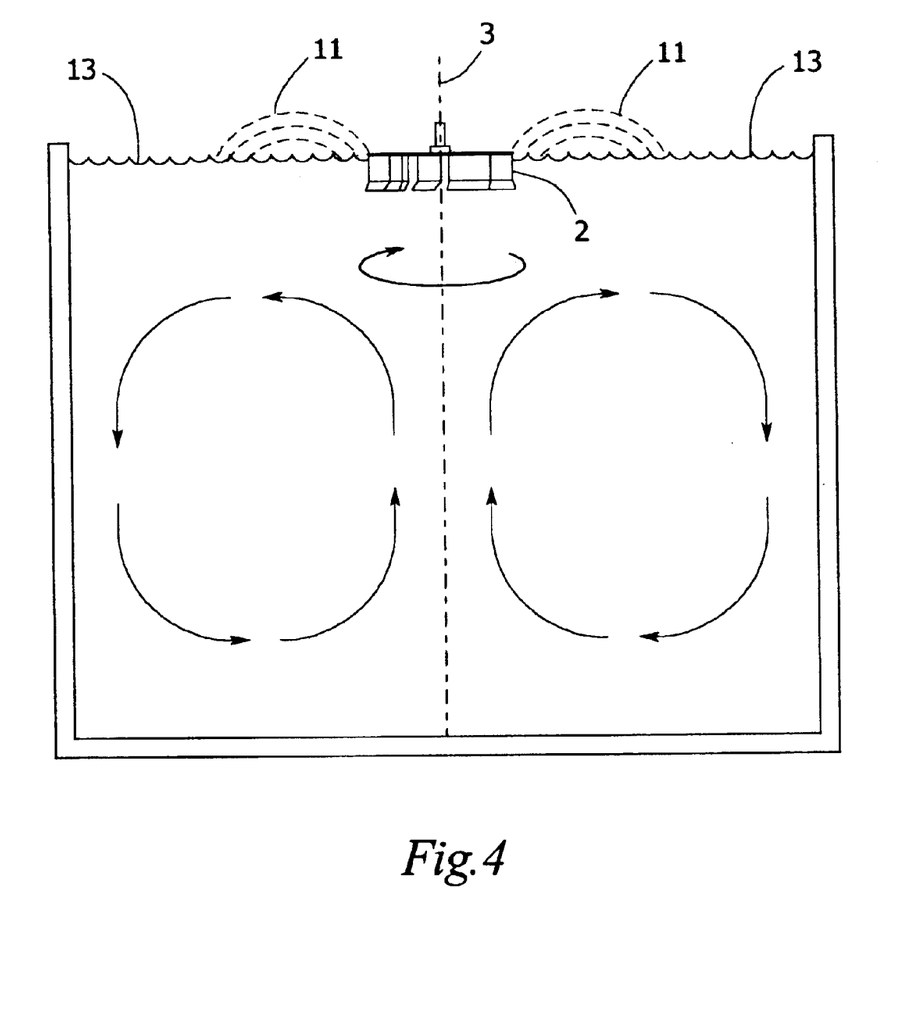
FIG. 4 shows the surface aeration impeller in operation in a tank.

These two distinctly different mechanisms or zones are created by all generic types of mechanical surface aerators. The liquid spray mass transfer zone 11 is created in the immediate gas space surrounding the periphery of the surface aeration impeller where the liquid is discharged into the surrounding gas at high velocity. The surface reaeration mass transfer zone 13 exists primarily outside the spray umbrella and in the bulk liquid near the surface in the area that is circumferential to the periphery of the liquid spray mass transfer zone. The two zones are indicated in FIG. 4. The liquid spray mass transfer zone can be reasonably characterized and modeled as a single-stage gas-liquid contacting zone wherein the liquid is dispersed into a virtually infinite, continuous gas phase of constant gas composition above the liquid surface. In contrast, the mechanism in the surface reaeration mass transfer zone is predominately characterized by oxygen transfer to a highly turbulent liquid surface containing entrained gas from the gas phase above the liquid surface. As the liquid spray zone impinges on the liquid surface of the tank, substantial gas bubble entrainment into the surface is accomplished and a "white-water" effect is produced at the periphery of the liquid spray impingement on the surface of the tank liquid. The surface reaeration mass transfer zone also includes the oxygen transfer to the highly turbulent liquid surface beneath the spray umbrella and thus includes all oxygen transfer to the surface liquid due to bubble entrainment and contact of the highly turbulent liquid surface with the gas above the liquid surface.

In contract to generally perceived prior opinion regarding the primary oxygen transfer mechanism of surface aerators, the present inventors have quantitatively shown that about two-thirds of the oxygen transfer of surface aerators occurs in the surface reaeration mass transfer zone and only about one-third in the liquid spray mass transfer zone. This suggests that impeller designs that enhance oxygen transfer in the surface reaeration zone (e.g. by increasing turbulence and volume flow rates) may have a greater overall effect on the total oxygen transfer of the system than impeller designs that focus primarily on increasing oxygen transfer in the spray zone (e.g. by improving spray characteristics like height and distance). Thus, a greater understanding of the oxygen mass transfer mechanisms in surface aerators has allowed the present inventors to independently analyze the oxygen transfer process within these two distinctively separate mass transfer zones leading to the improved surface aerator impeller designs as disclosed in this application. These new designs pump more liquid per unit of horsepower input through the liquid spray mass transfer zone and into the surface reaeration zone and thereby maximize the total oxygen mass transfer efficiency of the overall surface aeration system.

Accordingly, the following are selected objects of various embodiments of the present invention:

It is an object of the present invention to provide an improved surface aeration impeller having improved gas transfer rates into the liquid particularly in the surface reaeration mass transfer zone of the system.

It is also an object of the present invention to enhance turbulence and gas entrainment at the liquid surface created by the liquid spray of a surface aeration system.

It is an object of the present invention to provide an improved surface aeration impeller having reduced torque and increased rotational speed leading to reduced costs for motor and gear transmission equipment to rotate the impeller.

It is also an object of the present invention to provide an improved impeller design having increased liquid pumping capacity and efficiency.

SUMMARY OF THE INVENTION

The invention is an improved surface aeration impeller for use in a liquid filled tank that has a free liquid surface and an enclosed or open gas space above the liquid surface in the tank. The impeller is rotatable about an axis perpendicular to the static liquid surface. The impeller has a plurality of blades mounted on the underside of a disc or disc-like surface. Each blade has a multi-faceted or curved geometry ranging from vertical at the point of attachment to the disc to partially inclined at the bottom. The blades are spaced circumferentially about the axis and are disposed radially or at acute angles to radial lines from the axis of rotation of the impeller. The lower portions of the blades, which are less inclined or less vertical than the upper portions, are positioned below the static liquid surface. When the impeller is rotated, the lower portion of the impeller blade pumps the liquid up onto the vertical portion of the blades where the liquid is discharged into a spray umbrella in a direction upwardly from the static liquid surface and outwardly away from the rotating impeller.

DETAILED DESCRIPTION OF THE INVENTION

As mentioned above, approximately two-thirds of the oxygen transfer in a surface aeration system occurs in the surface reaeration mass transfer zone 13 while only about one-third occurs in the liquid spray mass transfer zone 11. Further, maximum efficiency of a surface aeration system is not maximized by simply increasing the discharge velocity or distance of travel of liquid spray in the liquid spray mass transfer zone as many prior art designs have assumed. This discovery has led the present inventors to focus on surface aerator designs that maximize the total oxygen transfer efficiency in both mass transfer zones with a particular emphasis on the surface reaeration mass transfer zone. This focus has led to surface aerator designs that operate significantly different that most prior art designs. In the present invention, the discharge velocity of the spray from the surface aeration impeller is much lower than most state-of-the-art surface aeration impellers. This results in a liquid spray that does not travel as high or as far as current commercial designs. For example, in preferred embodiments of the present invention the liquid spray travels only about 8 to 12 feet from the tip of the aerator impeller whereas current state-of-the-art surface aerators operate with a spray distance of about 15 to 18 feet or more from the tip of the impeller. However, while the spray of the present invention travels a shorter distance, much more liquid is pumped through the liquid spray mass transfer zone per unit of horse power input. This is a result of the lower discharge velocity of the liquid spray from the tip of the impeller. The increased liquid flow also creates much more liquid flow and much more turbulence in the surface reaeration mass transfer zone thus greatly increasing the oxygen transfer rate in the reaeration zone. This oxygen transfer increase in the surface reaeration zone more than compensates for any reduction in oxygen transfer rate within the liquid spray zone. Accordingly, the surface aeration impellers of the present invention are designed in a way that maximize the volume of liquid flow through the liquid spray and surface reaeration zones per unit of power input. This result is accomplished by dramatically increasing the up-pumping capability of the surface aeration impeller.

Thus, the surface aerator designs of the present invention have at least four primary advantages that distinguish them over the prior art. These four primary advantages are:

1. The invention provides more liquid pumping and the spraying of more liquid per unit of horsepower.
2. The invention provides higher oxygen transfer energy efficiency (SAE).
3. The invention provides better overall tank mixing and higher tank bottom velocities for improved biomass solids suspension.
4. The invention operates at higher speed and lower torque which reduces the equipment cost (gear reducer) while simultaneously providing all of the above advantages.

Figure 1:
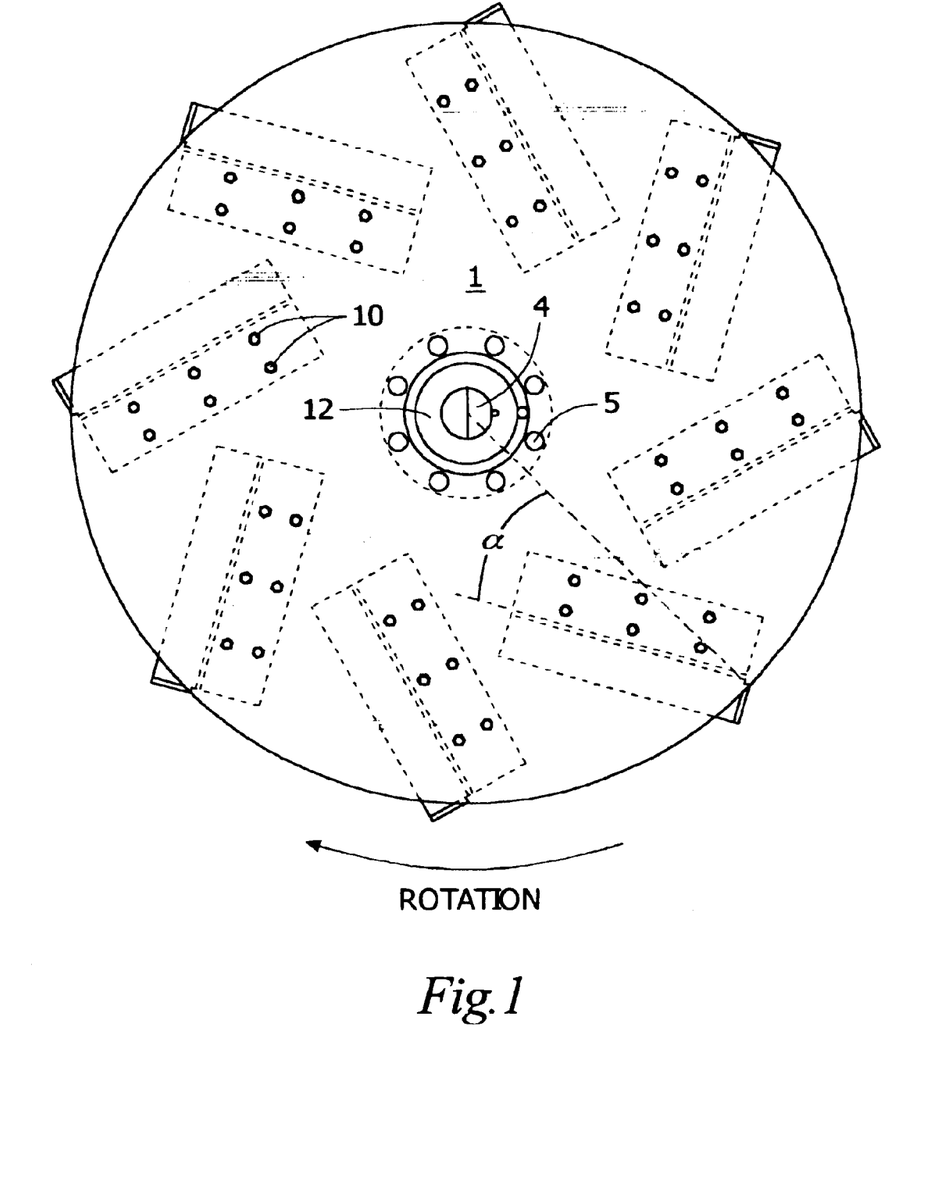
FIG. 1 is a top plan view of a preferred impeller design according to the present invention.

Referring to the Figures, there is shown in FIG. 1 a top view of an improved surface aeration impeller according to the present invention. The impeller has a plurality of vertically extending blades 2 attached to the underside of a rotatable disc or disc-like mounting member 1. Each blade in the embodiment shown in FIG. 1 is disposed at an angle ($\alpha$) of approximately 30–38° to a successive, circumferentially spaced radial line around the axis 3 of the impeller. In the example shown in FIG. 1 there are eight blades spaced 45° apart. The blades 2 are more clearly shown in FIG. 2 which is an isometric view of the impeller. These blades have substantially vertical portions 6 at the upward sections thereof. The blades 2 also have a non-vertical and non-horizontal lower section 7 which extends downwardly and outwardly in the direction of rotation of the impeller. This downwardly direction forms angle $\beta$ with the horizontal as shown in FIG. 3(A). The lower portion 7 of the blades acts as up-pumping pitched blade turbines to provide a high volume of liquid flow to the vertical upper portion 6 of the turbine blade which creates the liquid spray umbrella and liquid spray mass transfer zone 11.

Figure 2:
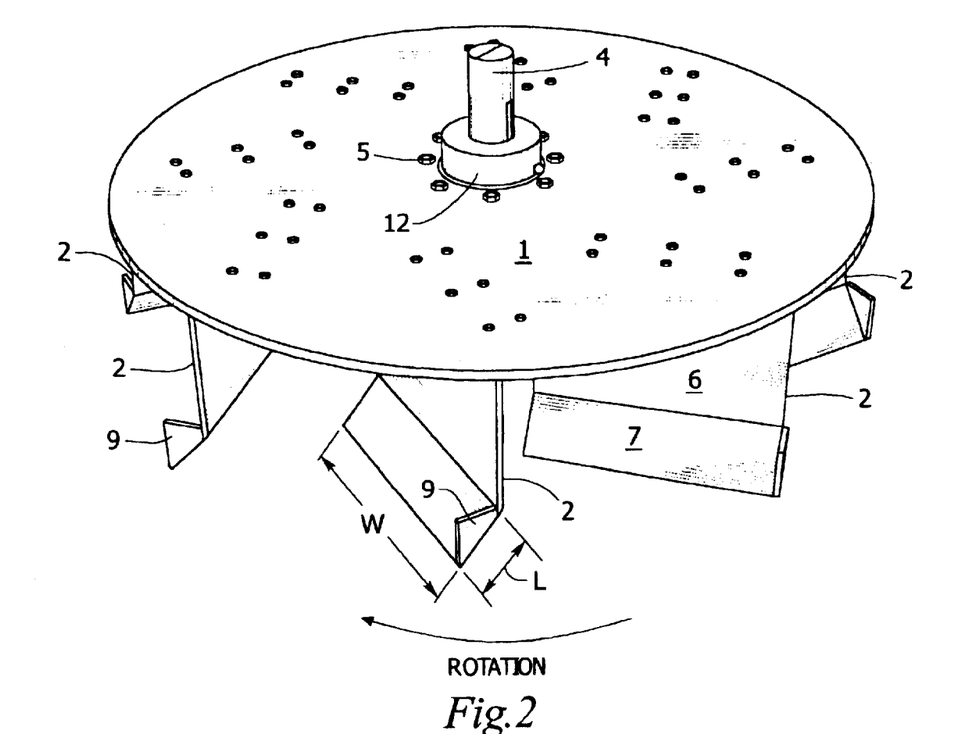
FIG. 2 shows an isometric view of an impeller in accordance with this invention.
Figure 3A:
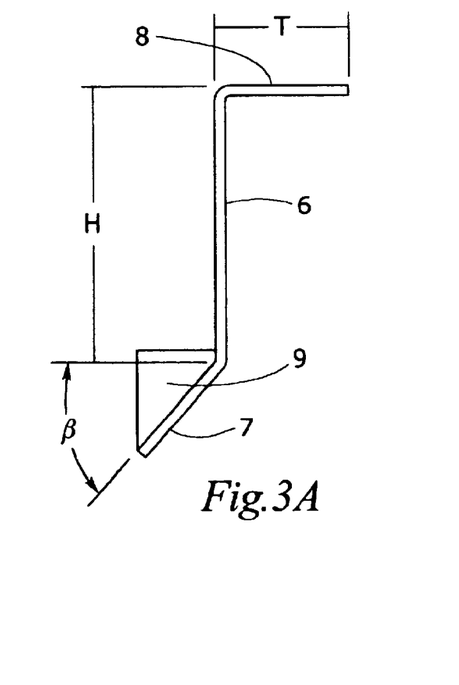
FIG. 3(A) is a profile view of a single blade with an endcap on the trailing edge.

The blades 2 in the present invention consist of at least two sections as shown in FIG. 2: (1) the generally vertical upper portion 6 and (2) the non-vertical but inclined lower portion 7. In FIG. 3 a third section, the top or mounting section 8, is also shown, but is optional. This top section is generally horizontal and contains holes for bolting 10 through corresponding holes in the mounting disc 1. This section is optional as other means of mounting the blades to the disc are possible. For example, the vertical section 6 could be directly welded to the mounting disc 1 or the vertical section 6 could be mounted directly to a vertical flange on the mounting disc. These types of blades are similar in shape to those on pitched blade turbine mixing impellers.

For ease of manufacturing and mounting, the inventors have found that a generally rectangular shape for all of these sections works well, though other shapes are certainly useable. In a preferred embodiment of the invention, the blades are made from a single rectangular piece of metal that has been creased in two positions. One crease is at a 90-degree angle and occurs near the top edge of the blade to provide the horizontal top portion 8 for easy mounting to the underside of the mounting disc 1 and a substantially vertical upper section 6. The second crease on this embodiment occurs approximately two-thirds to three-forths of the way down the length of the entire rectangular piece of metal. This crease provides for the downward and outwardly (in the direction of rotation) extending lower section of the blade 7. The second crease forms angle $\beta$ shown in FIG. 3(A). The angle $\beta$ is from about 20° to about 60°, preferably about 30° to 50°, and most preferably is about 35 to 45°.

Figure 3B:
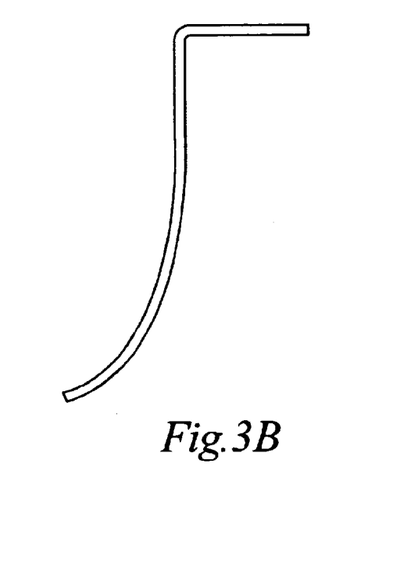
FIG. 3(B) shows the profile of a curved blade used in one embodiment of the present invention.

In a preferred embodiment of the invention the point at which the upper section of the blades meets the mounting member is a straight line (i.e. the upper section of the blades are straight in the horizontal plane). In another preferred embodiment, all sections of the blades are planar (e.g. rectangular or trapezoidal), and are thus non-curved. Also the outer edge of the upper section is typically contiguous with the outer edge of the disc-shaped mounting member. While the inventors have found rectangular shaped blades most desirable, other shapes are useable without diverting from the spirit of the invention. It is important for the blades to begin at the top with a substantially vertical section and end with an outwardly facing (in the direction of rotation) non-vertical section that will lie at least partially under the static liquid surface. The incline and size of this lower portion is such that it is sufficient to provide a substantial amount of upward pumping flow of liquid onto the vertical section when the impeller is rotated. These requirements can be met with the two-section blade described above as well as by a multi-sectioned (more than two) blade and a continuously curved blade as shown in FIG. 3B. Such continuously curved blades can be termed "airfoil" shaped as described in U.S. Pat. No. 5,988,604, especially FIG. 6 (incorporated by reference). The blades of the invention (both curved and non-curved) preferably have an approximately constant width W along their entire length. Such blades can be made relatively easily from a single rectangular piece of material (e.g. stainless steel).

The number of blades on the surface aeration impeller of the present invention is generally in the range of about 6 to 12. The optimal number of blades will depend on the specific application, however, smaller diameter impellers will generally have fewer blades and larger diameter impellers typically have 8 or more blades. In preferred embodiments the number of blades is about 6–8 and in an even more preferred embodiment there are exactly 8 blades.

The positioning of the blades is important but can also vary considerably. The inventors have found that positioning the blades radially under the disc-shaped mounting member produces a surface aeration impeller that out performs all prior art designs. However, the inventors have also discovered that positioning the blades non-radially—i.e. they do not project radially outward from the axis perpendicular to the static liquid surface—produces a surface aeration impeller with even greater liquid pumping capability and oxygen transfer efficiency. In this non-radial embodiment, the inner edge of the vertical section of the blade is pushed forward in the direction of rotation forming a non-zero angle ($\alpha$) where a is defined as the angle between a radial line (through the outer edge of the vertical section) and the top edge of the vertical section 6 of the blade (see FIG. 1). This angle is typically between 20° and 60°, preferably between about 25° and 50° and most preferably is about 30–45°. Another way of characterizing the positioning of the blades is that they are "swept back" or "off-axis" (i.e. non-radial). It is worth noting that in the non-radial version of the present invention there are no imaginary radial lines that lie on the surface of any blade section. In other words, there are no lines lying on the surface of any blade section which are also radial lines.

The size of the blades may also vary considerably. Referring to the figures, the width W of the blades are within the range of about 0.1 to 0.4 the diameter d of the disc. Preferably W is less than $\frac{1}{3}$ d and most preferably is about 0.2 to 0.3 d. The height H of the vertical section of the blades are within the range of 0.05–0.25 d, preferably 0.1–0.2 d. The length L of the lower section of the blade is typically less than the height of the vertical section. Length L can be from 0.03–0.2 d, preferably less than 0.1 d or about 0.05 d. Finally, the width T of the optional top section 8 for mounting onto the disc is not critical as long as it allows for adequate mounting, for example by bolts.

The blades of the invention have an optional additional segment known as an endcap. The endcap 9 is shown in FIGS. 2 and 3(A). The endcap is a relatively flat geometric piece positioned essentially perpendicular to the vertical section 6 and connects the outer or trailing edges of both the vertical section 6 and the lower section 7. While the exact shape of the endcap can vary widely, the critical feature of the endcap is that it prevents liquid from flowing or "sliding" off the trailing edge of the blades below the vertical section 6 and simultaneously enhances the uplifting or up-pumping capability of the impeller. The inventors have found that an endcap can significantly increase the power delivered and simultaneously increase the standard aeration efficiency as the examples below demonstrate.

The blades 2 of the invention are mounted on the underside of a disc 1 or a disc-like mounting member for mounting onto a shaft 4 that provides axial rotation. The disc provides a convenient method for positioning the blades radially or at an acute angle a as described above. The term disc-like is meant to include any rotatable mounting member having at least a top surface and a bottom surface and capable of attaching to the vertical section of the blades radially or at an angle a on a bottom surface. Included in the term "disc-like" are discs with a saw-toothed shaped edge and spoke and ring type structures.

Means for attaching the entire impeller (disc and blades) to the shaft is not strictly part of the present invention as such means are well known to those skilled in the art of impellers. In a preferred embodiment, the mounting member is substantially a disc with a hole in the center for receiving and connecting to a rotatable shaft 4 using an attachment means 12 which is attached to the disc with bolts 5 and to the shaft with pins.

The overall diameter of the impellers according to the invention will depend on the specific application. In the case of sewage or wastewater aeration, typical diameters will be from about 50 to 100 inches. In other applications, the diameter could be much smaller, especially if the tank size is smaller. The size of the impeller is largely determined by the power required to meet the specific process requirements (i.e. the oxygen transfer rate) but can also be influenced by the size and configuration of the tank in which it is employed.

EXAMPLES

Impellers substantially as shown in FIG. 1 were made and tested in a 49 feet by 49 feet square tank containing about 17 feet of static liquid which corresponds to about 320,000 gallons of water. The test involved mounting the impeller on a vertical shaft connected to a power source and gear reduction means. All the impellers used in the examples below contained 8 blades and the overall impeller diameter was 76.25 inches. Additionally, all blades tested had a width W of 20.5 inches and an upper/vertical section height H of 12.5 inches. The horsepower used in the examples ranged from about 30 to 85 HP. The primary variables were: (1) the "off-axis" angle $\alpha$, (2) the inclined lower section angle $\beta$, (3) liquid submergence, where submergence is defined as the static liquid level in inches above the intersection of the vertical and lower sections of the blades, (4) length L of the lower section 7, and (5) the presence or not of an endcap 9.

Results were primarily determined by calculation of the standard aeration efficiency (SAE) where SAE is defined as the number of pounds of oxygen transferred into the liquid per hour per horsepower of energy used to operate the aeration system. These tests and calculations were made by using the ASCE standard procedure for determining the SOTR (standard oxygen transfer rate) at 20° C. liquid temperature and 1 atm pressure. The results shown for more than one run are given as the average SAE for all runs.

Example 1

This example illustrates one embodiment of the invention with an impeller according to FIG. 1 having a equal to 30°, $\beta$ equal to 30° and a blade with dimensions H=12.5, W=20.5, and L=12.0 inches. The blade also has an endcap. The top of the endcap was approximately one inch above the crease defining the intersection of the upper and lower sections of the blades. The results (in SAE) show very good efficiency with little effect on the oxygen transfer efficiency of operating the impeller at various submergence levels.

| α | β | L | Submergence | Endcap | # Runs | SAE |
|---|---|---|---|---|---|---|
| 30° | 30° | 12 in | 0.0 in | Yes | 3 | 3.39 |
| 30° | 30° | 12 in | 4.0 in | Yes | 3 | 3.40 |
| 30° | 30° | 12 in | 7.0 in | Yes | 2 | 3.32 |

Example 2

This example uses the same impeller as demonstrated in Example 1 with the exception that the endcap was removed. The results (in SAE) show much lower lower efficiency with some effect of operating the impeller at various submergence levels. The SAE results of these two examples clearly show the dramatic improvement in oxygen transfer efficiency possible with the use of the endcap as in Example 1. Additionally, it should be noted that we were able to get much more power input into Example 1 in addition to the improved SAE results.

| α | β | L | Submergence | Endcap | # Runs | SAE |
|---|---|---|---|---|---|---|
| 30° | 30° | 12 in | 1.0 in | No | 2 | 2.43 |
| 30° | 30° | 12 in | 3.0 in | No | 1 | 2.74 |
| 30° | 30° | 12 in | 5.0 in | No | 2 | 2.92 |

Example 3

This example uses the same impeller as demonstrated in Example 1 with the exception that the length of the lower section was reduced from 12 inches to 8 inches. The results (in SAE) show improved efficiency over prior art designs currently advertised with SAE of about 3.3. The SAE results also clearly show that a smaller 8 inch lower blade section length gives higher transfer efficiencies than a 12 inch section for this configuration.

| α | β | L | Submergence | Endcap | # Runs | SAE |
|---|---|---|---|---|---|---|
| 30° | 30° | 8 in | 0.0 in | Yes | 3 | 3.56 |
| 30° | 30° | 8 in | 2.5 in | Yes | 1 | 3.78 |
| 30° | 30° | 8 in | 5.5 in | Yes | 3 | 3.79 |
| 30° | 30° | 8 in | 7.8 in | Yes | 1 | 4.11 |

Example 4

This example is similar to Example 2 except that the lower section inclination angle β is increased to 45° and the length of the lower section 7 of the blade is reduced to 7 inches. The results (in SAE) are significantly improved over Example 2 teaching that in this configuration a larger P and shorter lower section L provide increased oxygen transfer efficiency. Again this example suggests a general trend of increasing oxygen transfer efficiency with increasing liquid submergence values.

| α | β | L | Submergence | Endcap | # Runs | SAE |
|---|---|---|---|---|---|---|
| 30° | 45° | 7 in | 4.0 in | No | 3 | 3.66 |
| 30° | 45° | 7 in | 6.0 in | No | 2 | 3.97 |
| 30° | 45° | 7 in | 7.5 in | No | 3 | 4.02 |
| 30° | 45° | 7 in | 9.5 in | No | 1 | 4.09 |

Example 5

This example is the same as Example 4 with the additional of an endcap having its top edge 1 inch above the crease where the vertical and lower sections meet. The results again are generally excellent with SAE above 4. The addition of an endcap shows some improvement in oxygen transfer efficiency compared with the corresponding example without an endcap.

| α | β | L | Submergence | Endcap | # Runs | SAE |
|---|---|---|---|---|---|---|
| 30° | 45° | 7 in | 7.9 in | Yes | 1 | 4.20 |
| 30° | 45° | 7 in | 8.6 in | Yes | 1 | 4.28 |
| 30° | 45° | 7 in | 9.0 in | Yes | 2 | 4.35 |

Example 6

This example is similar to Example 5 except that the lower blade length L was decreased to 4 inches. This impeller also gave excellent efficiency values consistently above 4.0 for various submergence values.

| α | β | L | Submergence | Endcap | # Runs | SAE |
|---|---|---|---|---|---|---|
| 30° | 45° | 4 in | 7.4 in | Yes | 1 | 3.97 |
| 30° | 45° | 4 in | 8.4 in | Yes | 1 | 4.26 |
| 30° | 45° | 4 in | 9.5 in | Yes | 1 | 4.34 |
| 30° | 45° | 4 in | 10.2 in | Yes | 1 | 4.20 |

Example 7

The impeller used in this example is the same as that used in Example 6 except that the "off-axis" angle α was changed to 38° instead of 30°. This impeller also gave excellent efficiency values which were significantly and consistently above 4.0 for most submergence levels.

| α | β | L | Submergence | Endcap | # Runs | SAE |
|---|---|---|---|---|---|---|
| 38° | 45° | 4 in | 7.0 in | Yes | 2 | 4.00 |
| 38° | 45° | 4 in | 8.5 in | Yes | 1 | 4.10 |
| 38° | 45° | 4 in | 9.0 in | Yes | 1 | 4.21 |
| 38° | 45° | 4 in | 10.8 in | Yes | 1 | 4.31 |
| 38° | 45° | 4 in | 12.3 in | Yes | 1 | 4.23 |

Example 8

The impeller used in this example was the same as Example 7 except that the blades were positioned radially. That is the top edge of the upper vertical section was connected to the underside of the disc mounting member in a radial manner. These results suggest that the radial embodiment of the invention can produce SAEs better than the best state-of-the-art results of about 3.3 SAE. However, the radial embodiment does not perform as well as the comparable non-radial impeller embodiment described above.

| α  | β   | L    | Submergence | Endcap | # Runs | SAE  |
|----|-----|------|-------------|--------|--------|------|
| 0° | 45° | 4 in | 2.5–4.0 in  | Yes    | 3      | 3.57 |
| 0° | 45° | 4 in | 6.0–6.5 in  | Yes    | 2      | 3.80 |
| 0° | 45° | 4 in | 9.0–9.5 in  | Yes    | 3      | 3.77 |
| 0° | 45° | 4 in | 10.5–11.5 in| Yes    | 3      | 3.33 |

These examples dramatically demonstrate the improved oxygen transfer efficiency of the present invention over a wide variety of embodiments. State-of-the-art surface aeration impeller designs produce standard aeration efficiencies of about 3.3 over the same range of operating conditions used herein while the present invention consistently produces standard aeration efficiencies well above 3.3 and well above 4.0 for certain non-radial embodiments of the invention. Additionally, the present inventors have confirmed the higher pumping capacity performance of the invention compared with prior art surface aeration impeller designs. With the present impeller design liquid flow velocities throughout the aeration tank are significantly increased. This improves overall bulk liquid mixing (illustrated in FIG. 4) and can even eliminate the need for bottom mixing impellers to increase bottom fluid velocities in some applications.

While the invention has been particularly shown and described with reference to preferred embodiments thereof, it will be understood by those skilled in the art that various alterations in form and detail may be made therein without departing from the spirit and scope of the invention. In particular, while the invention illustrated by the figures shows a specific position, size, and shape of the blades on the impeller of the invention, these parameters may be varied within the scope of the invention as described herein. Further, the means of attaching the blades to an axially mountable member to provide for axial rotation of the impeller can vary considerably and is not limited by the preferred embodiments described herein and depicted in the figures.

Additionally, while this application generally addresses the use of surface aeration impellers in the treatment of wastewater, the use of such impellers are by no means limited to this application. Surface aeration impellers like those of the present invention can be used in a variety of industrial applications where improved aeration is desirable. One particular example in addition to sewage treatment is aeration in bio-reaction processes. These processes include fermentation by circulating slurries containing microbes and growth media. The present invention enables improved oxygenation and mixing of such liquids to promote the fermentation process.

What is claimed is:

1. A surface aeration impeller designed to rotate about an axis perpendicular to a static liquid surface, said impeller comprising a plurality of blades attached to the underside of a generally disc-shaped mounting member, said mounting member being parallel to said static liquid surface when mounted on a shaft for rotation about said axis;

wherein said impeller blades comprise an upper generally vertical section attached to the underside of said disc-shaped mounting member, said vertical section having a generally rectangular surface with a lower inclined generally rectangular section attached to the lower edge thereof that extends downwardly and outwardly in the direction of rotation and is of a size sufficient to provide a substantial upward pumping flow of liquid onto the vertical section when said impeller is rotated.

2. The surface aeration impeller according to claim 1 wherein said upper section of said blades is planar and positioned radially with respect to the axis of rotation.

3. The surface aeration impeller according to claim 1 wherein said upper section is planar and positioned non-radialy with respect to the axis of rotation.

4. The surface aeration impeller according to claim 3 wherein said planar upper generally vertical section of said impeller blades is mounted non-radially with respect to the axis of rotation such that an angle α is formed between an imaginary radial line from the axis of rotation and through the top outer edge of the upper section and a line formed by the top edge of said upper section; and wherein said angle α is between about 20° to 60°.

5. The surface aeration impeller according to claim 4 wherein said lower inclined section of each blade forms an angle β with respect to said generally disc-shaped mounting member; and wherein α and β are from about 30° to 50°.

6. The surface aeration impeller according to claim 5 wherein α is from about 30° to 45° and β is from about 35° to 50°.

7. The surface aeration impeller according to claim 1 wherein said lower inclined section of each blade forms an angle β with respect to said generally disc-shaped mounting member; and wherein β is from about 20° to 60°.

8. The surface aeration impeller according to claim 1 having from 6 to 12 blades.

9. The surface aeration impeller according to claim 8 having about 8 or more blades.

10. The surface aeration impeller according to claim 1 wherein said upper and lower sections of said impeller blades are planar and substantially rectangular shaped and have width W from 0.1 to 0.4 d; and wherein said upper section has height H from 0.05 to 0.25 d and said lower section has length L from 0.03 to 0.2 d, wherein d is the diameter of the disc shaped mounting member.

11. The surface aeration impeller according to claim 10 wherein the ratio L 1 H is from about 0.32 to 0.64.

12. The surface aeration impeller according to claim 10 wherein W is less than ⅓ d, H is from 0.1 to 0.25 d, and L is from 0.05 to 0.1 d.

13. The surface aeration impeller according to claim 10 wherein said upper section has height H>0.1 d and wherein the ratio L 1 H is from about 0.32 to 0.64.

14. The surface aeration impeller according to claim 1 wherein said blades additionally contain an endcap.

15. The surface aeration impeller according to claim 14 wherein the vertical height of the endcap at the point of attachment to the upper section is less than about ¼ H wherein H is the height of the upper section.

16. The surface aeration impeller according to claim 1 wherein said upper section of said blades has a curvilinear top edge.

17. A surface aeration impeller designed to rotate about an axis perpendicular to a static liquid surface, said impeller comprising a plurality of blades attached to the underside of a generally disc-shaped mounting member, said mounting member being parallel to said static liquid surface when mounted on a shaft for rotation about said axis;

wherein said blades are continuously curved downwardly and outwardly in the direction of rotation and begin at the top with a substantially vertical section and end with an outwardly facing non vertical section that will lie at least partially under the liquid surface and is sufficient in size and shape to provide a substantially upward pumping flow of liquid when the impeller is rotated.

18. The surface aeration impeller according to claim 17 wherein said blades additionally contain an endcap.

19. A surface aeration impeller designed to rotate about an axis perpendicular to a static liquid surface, said impeller comprising a plurality of blades attached to the underside of a generally disc-shaped mounting member, said mounting member being parallel to said static liquid surface when mounted on a shaft for rotation about said axis;

wherein said blades comprise an upper generally vertical section having a top edge connected to said disc-shaped mounting member and a bottom edge coupled to a lower inclined section that extends downwardly and outwardly in the direction of rotation;

and wherein said bottom edge of said upper generally vertical section is substantially parallel to said disc-shaped mounting member.

20. A surface aeration impeller designed to rotate about an axis perpendicular to a static liquid surface, said impeller comprising a plurality of blades attached to the underside of a generally disc-shaped mounting member, said mounting member being parallel to said static liquid surface when mounted on a shaft for rotation about said axis;

wherein said blades comprise an upper generally vertical section and a lower inclined section that extends downwardly and outwardly in the direction of rotation; and wherein said blades contain an endcap.

* * * * *